United States Patent
Jeffrey et al.

(10) Patent No.: US 10,603,455 B2
(45) Date of Patent: Mar. 31, 2020

(54) MEDICO-SURGICAL TUBE AND FLANGE ASSEMBLIES

(71) Applicant: SMITHS MEDICAL INTERNATIONAL LIMITED, Ashford (GB)

(72) Inventors: Andrew Thomas Jeffrey, Hythe (GB); Christopher John Woosnam, Great Sutton (GB)

(73) Assignee: SMITHS MEDICAL INTERNATIONAL LIMITED, Ashford, Kent (GB)

( * ) Notice: Subject to any disclaimer, the term of this patent is extended or adjusted under 35 U.S.C. 154(b) by 355 days.

(21) Appl. No.: 15/543,262

(22) PCT Filed: Dec. 15, 2015

(86) PCT No.: PCT/GB2015/000327
§ 371 (c)(1),
(2) Date: Jul. 13, 2017

(87) PCT Pub. No.: WO2016/116721
PCT Pub. Date: Jul. 28, 2016

(65) Prior Publication Data
US 2017/0368284 A1 Dec. 28, 2017

(30) Foreign Application Priority Data
Jan. 24, 2015 (GB) .................................. 1501209.9

(51) Int. Cl.
*A61M 16/04* (2006.01)
(52) U.S. Cl.
CPC .... *A61M 16/0488* (2013.01); *A61M 16/0465* (2013.01); *A61M 16/0497* (2013.01)

(58) Field of Classification Search
CPC .............. A61J 17/001; A61M 16/0427; A61M 16/0429; A61M 16/0465; A61M 16/0488;
(Continued)

(56) References Cited

U.S. PATENT DOCUMENTS

| | | | | | |
|---|---|---|---|---|---|
| 2,693,182 | A | * | 11/1954 | Phillips | A61M 16/0488 128/200.26 |
| 2,820,457 | A | * | 1/1958 | Phillips | A61M 16/0488 128/200.26 |
| 3,688,774 | A | * | 9/1972 | Akiyama | A61M 16/0465 128/200.26 |
| 3,884,447 | A | * | 5/1975 | Alexander | F16K 1/40 251/144 |

(Continued)

FOREIGN PATENT DOCUMENTS

| | | |
|---|---|---|
| GB | 2 028 139 A | 3/1980 |
| GB | 2 102 490 A | 2/1983 |
| WO | 2006/087513 A1 | 8/2006 |

OTHER PUBLICATIONS

PCT International Search Report and Written Opinion, dated Mar. 1, 2016, PCT/GB2015/000327.

*Primary Examiner* — Annette Dixon
(74) *Attorney, Agent, or Firm* — Louis Woo

(57) ABSTRACT

A tracheostomy tube (1) has a movable and lockable flange (2) by which the tube can be supported about the neck of a patient. The flange has a rotatable locking ring (34), which is threaded with a housing (26) fixed with the wings (22 and 23) of the flange. A resilient sleeve (50) is located in a recess (44) of the locking ring between a compression surface (45) on the locking ring at one end and the floor (46) of the housing at the opposite end. When the locking ring (34) is twisted it is moved forwardly along the housing (26), thereby compressing the resilient sleeve (50) axially. The axial compression causes the sleeve (50) to expand radially against the outside of the tube (1) and the inside of the housing (26), thereby locking the flange (2) in position.

10 Claims, 2 Drawing Sheets

(58) Field of Classification Search
CPC .......... A61M 16/0493; A61M 16/0497; A61M 16/0434; A61M 16/0468; A61M 16/047; A61M 16/0472; A61M 16/0683; A61M 16/0816; A61M 16/1045; A61M 2025/0206; A61M 2025/0213; A61M 2025/022; A61M 2025/024; A61M 2025/0253; A61M 2025/026; A61M 2205/7518; A61M 2205/7527; A61M 2210/0625; A61M 2230/005; A61M 25/02; F16K 1/40; F16K 15/145; F42B 19/24; H01M 2/40; H01M 6/34; Y10S 128/26; Y10S 128/912; Y10S 251/902; Y10S 128/15; Y10T 137/7879; B01D 39/1623; B01D 39/18; B01D 39/2055

See application file for complete search history.

(56) References Cited

U.S. PATENT DOCUMENTS

| | | | | |
|---|---|---|---|---|
| 4,235,229 A | * | 11/1980 | Ranford | A61M 16/0465 128/207.17 |
| 5,146,913 A | * | 9/1992 | Khorsandian | A61M 16/0488 128/200.26 |
| 5,251,616 A | * | 10/1993 | Desch | A61M 16/0465 128/200.26 |
| 2008/0142003 A1 | | 6/2008 | Depel | |
| 2011/0023875 A1 | | 2/2011 | Ledwith | |
| 2013/0289722 A1 | | 10/2013 | Leibitzki et al. | |
| 2014/0261441 A1 | | 9/2014 | Phillips et al. | |

* cited by examiner

MEDICO-SURGICAL TUBE AND FLANGE ASSEMBLIES

FIELD OF INVENTION

This invention relates to medico-surgical tube assemblies of the kind including a tube and a flange assembly movable along the length of the tube.

BACKGROUND OF INVENTION

Medico-surgical tubes, such as tracheostomy tubes, are commonly provided with a flange to secure the tube to the patient's body. In the case of a tracheostomy tube, the flange is positioned close to the surface of the neck where the tube enters the tracheostomy, a tape being threaded through openings in the flange and fastened around the neck. For most patients, a comfortable fit can be achieved using one of a range of several different size tubes, each having a flange mounted at a fixed location along the tube suitable for patients having an average anatomy. There are, however, some situations where a fixed flange is not suitable, such as, for example, in obese patients where tissue between the neck surface and the trachea is very thick. In these situations, it is preferable for the flange to be movable along the tube to the ideal position and to be lockable in that position. Tubes with adjustable flanges are described in, for example, U.S. Pat. Nos. 5,026,352, 4,249,529, 4,449,527, 4,498,903, 4,530,354, 4,530,354, 4,649,913, 4,683,882, 4,774,944, WO80/02645, WO84/03217, U.S. Pat. No. 4,278,081 and WO06/087513. U.S. Pat. No. 8,104,476 describes a tube with an adjustable flange having two halves that clamped about the outside of a tube when a lever is folded flat. It is important to achieve a secure fastening of the flange to the tube even when this is wet and slippery. Because of this the flange must exert a relatively high frictional force on the outside of the tube. This can cause a problem in that the outside of the tube may be compressed by the flange, leading to a permanent or semi-permanent indentation in the outside of the tube, which may also cause a localised reduction in the diameter and cross-sectional area of the bore through the tube.

It is an object of the present invention to provide an alternative medico-surgical tube assembly and flange assembly for a medico-surgical tube assembly.

BRIEF SUMMARY OF INVENTION

According to one aspect of the present invention there is provided a medico-surgical tube assembly of the above-specified kind, characterised in that the flange assembly includes a locking arrangement including a sleeve of a resilient material extending in a recess of the locking arrangement and arranged to embrace a part of the length of the tube and a manually-operable member mounted with the locking arrangement and displaceable between a locking position and a released position, and that the manually-operable member is arranged, when in the released position, to allow free movement of the flange assembly along a part at least of the length of the tube and, when in the locking position, to apply an axial force to an end of the sleeve such that the sleeve is compressed axially and is thereby deformed inwardly into gripping contact with the outside of the tube sufficient to prevent the flange assembly moving along the tube.

The manually-operable member is preferably rotatable about the axis of the tube between the locking position and the released position. The manually-operable member may be a screw-threaded ring embracing the tube. The sleeve of resilient material may be of neoprene. The manually-operable member and the locking arrangement may be provided with cooperating detents arranged to retain the manually operable member in the locked position. The tube may be a tracheostomy tube and the flange assembly may have two wings projecting outwardly and each provided with a formation by which the opposite ends of a neck strap can be attached to the flange assembly.

According to another aspect of the present invention there is provided a medico-surgical tube assembly including a tube and a flange assembly movable along the length of the tube, characterised in that the flange assembly includes a locking arrangement including a housing having a base with an opening through which the tube extends and a cylindrical wall projecting axially of the tube from the base and having an inner surface formed with a screw thread and spaced from the tube, that the locking arrangement further includes a locking ring having an outer collar extending around the outside of the housing and an inner sleeve with a screw thread on its outer surface engaged with the screw thread on the cylindrical wall, that the locking ring defines a radially-extending compression surface and a recess between the inside of the sleeve and the outside of the tube, and that the locking arrangement includes a sleeve of resilient material located in the recess such that when the locking ring is rotated it moves axially towards the base and the compression surface engages an end of the sleeve of resilient material thereby to compress the sleeve axially and deform it inwardly into gripping contact with the outside of the tube sufficient to prevent the flange assembly moving along the tube.

According to a further aspect of the present invention there is provided a flange assembly for a medico-surgical tube, characterised in that the flange assembly includes a locking arrangement including a sleeve of a resilient material extending in a recess of the locking arrangement and arranged to embrace a part of the length of the tube and a manually-operable member mounted with the locking arrangement and displaceable between a locking position and a released position, and that the manually-operable member is arranged, when in the released position, to allow free movement of the flange assembly along a part at least of the length of the tube and, when in the locking position, to apply an axial force to an end of the sleeve such that the sleeve is compressed axially and is thereby deformed inwardly into gripping contact with the outside of the tube sufficient to prevent the flange assembly moving along the tube.

The manually-operable member is preferably a screw-threaded ring arranged to embrace the tube and rotatable about the axis of the tube between the locking position and the released position.

According to a fourth aspect of the present invention there is provided a flange assembly, which can be fitted onto and be movable along the length of a medico-surgical tube, characterised in that the flange assembly includes a locking arrangement including a housing having a base with an opening through which the tube can extend and a cylindrical wall projecting axially from the base and having an inner surface formed with a screw thread, that the locking arrangement further includes a locking ring having an outer collar extending around the outside of the housing and an inner sleeve with a screw thread on its outer surface engaged with the screw thread on the cylindrical wall, that the locking ring defines a recess between the inside of the sleeve and the outside of the tube and a radially-extending compression surface, and that the locking arrangement includes a sleeve of resilient material located in the recess such that when the locking ring is rotated it moves axially towards the base and the compression surface engages an end of the sleeve of resilient material thereby to compress the sleeve axially and deform it inwardly into gripping contact with the outside of the tube sufficient to prevent the flange assembly moving along the tube.

BRIEF DESCRIPTION OF THE DRAWINGS

A tracheostomy tube assembly according to the present invention will now be described, by way of example, with reference to the accompanying drawing, in which.

DETAILED DESCRIPTION OF INVENTION

Figure 1:
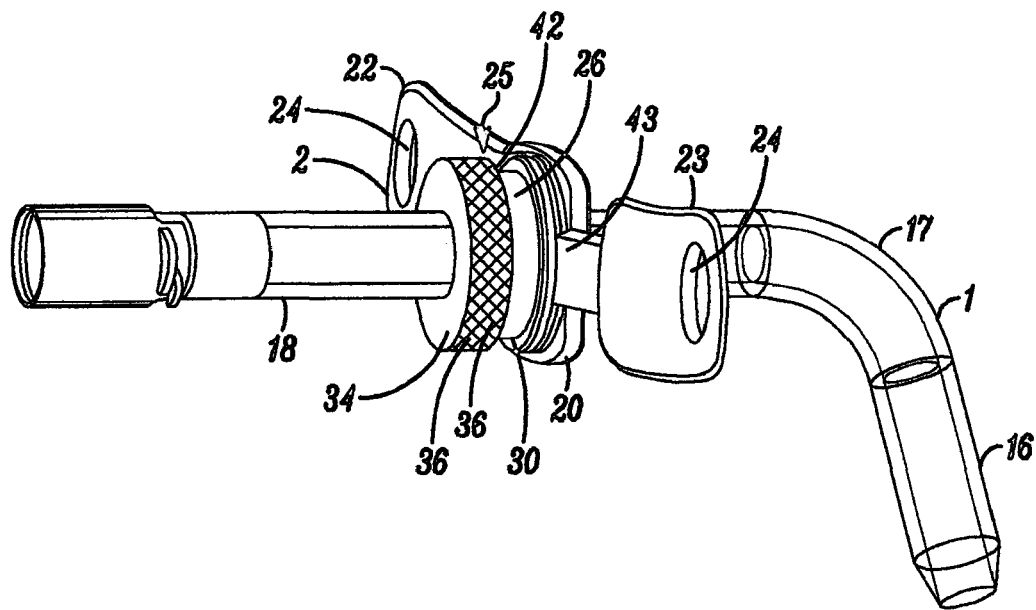
FIG. 1 is a perspective view of the assembly where the flange is unlocked.

With reference first to FIG. 1, the tube assembly comprises a tube 1 and a flange assembly 2 with a locking arrangement 25, the flange assembly being movable along the tube and lockable at different locations along its length.

The tube 1 is made of a conventional, bendable plastics material, such as PVC, polyurethane or silicone, is hollow with a circular section and has a smooth inner surface. The outer surface may also be smooth or it could be textured to improve the grip of flange assembly 2. The tube 1 may have a shaft reinforced with a helical wire or similar member. The tube 1 is illustrated as not having any sealing cuff but it will be appreciated that the invention could be applied to a tracheostomy tube with an inflatable or other form of conventional sealing cuff. Similarly, the tube could have other conventional features, such as provision for suctioning above a cuff, fenestrations to enable speech and the like. The shaft of the tube 1 comprises a straight patient end region 16, a curved intermediate region 17 and a straight machine end region 18 extending at substantially 120° to the patient end region. Alternative shape shafts are possible, such as shafts that are curved continuously along their length or shafts that have a natural straight shape but are highly flexible so that they can conform readily to the shape of the anatomy.

The flange assembly 2 has a rectangular central plate 20 with a central circular aperture 21 (FIG. 3) the diameter of which is such that the tube 1 is a close sliding fit within it. Two wings 22 and 23 extend from the central plate 20 on opposite sides. The two wings 22 and 23 are generally rectangular, being curved slightly along their length and are each formed with a lateral slot 24 towards their free end by which a tape, strap or the like can be secured to the wing. The two wings 22 and 23 are attached with the central plate 20 by respective flexure sections or webs 42 and 43 formed integrally with the plate and the wings. The webs 42 and 43 have a reduced width compared with the plate 20 and wings 22 and 23 to allow them to flex when the wings are pulled forwardly. This allows the wings 22 and 23 to hinge when they are pulled forwardly after positioning, for access, observation or cleaning of the region under the flange. The reduced width of the webs 42 and 43 also allows some rotational movement between the wings and the central plate, and hence the tube. This helps reduce the torque applied to the patient. The flange assembly 2 is also arranged such that the forward, patient side of the wings 22 and 23 is set forwardly relative to the forward side of the central plate 20 by 1-2 mm so as to reduce pressure on the stoma site. The wings 22 and 23 are further designed to be relative large in area so as to help reduce pressure on any one part of the neck anatomy, which may help reduce pressure sores. The large size of the wings 22 and 23 reduces the risk of the flange becoming lost in the skin folds present in patients with a larger neck mass.

Figure 3:
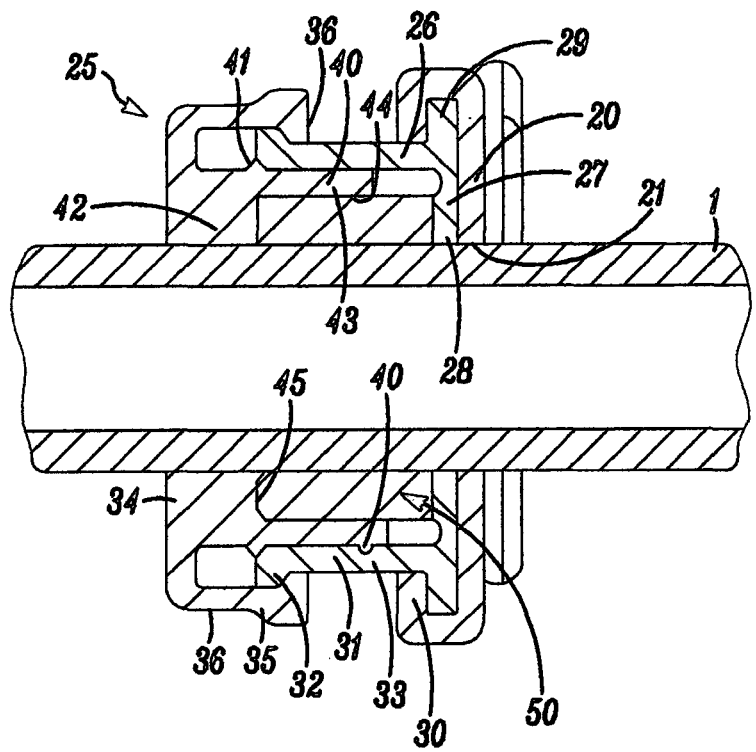
FIG. 3 is a cross-sectional side elevation of the flange in an unlocked state.

With reference now also to FIG. 3, which shows the locking arrangement 25 of the flange in a released or unlocked state, the locking arrangement has a housing 26 with a base 27 having a central opening 28 through which the tube 1 extends freely. The base 27 has an outwardly-projecting lip 29 around its edge that is trapped under a ledge 30 formed around the central plate 20 of the flange 2. The housing 26 also has a cylindrical wall 31 extending axially of the tube 1 and open at its left-hand, rear or machine end where it is formed with a narrow, outwardly-extending retaining lip 32. The outer surface of the wall 31 is smooth but its inner surface is formed with a screw thread 33 that makes a single turn between the outer and inner ends of the wall.

A manually-operable member in the form of a rotatable locking ring 34, being a part of the locking arrangement 25, is mounted on the base 27. The locking ring 34 has an outer collar 35 formed with knurls 36 or similar gripping formations around its outer surface. The collar 35 has a smooth inner surface of the same diameter as the outer diameter of the lip 32 around the wall 31, the right-hand, forward or patient end of the collar being formed with an inwardly-extending lip 36 arranged to engage the forward side of the lip around the wall when the ring 34 is in its unlocked, left, rearmost position, so as to prevent the ring coming away from the locking arrangement. The locking ring 34 also has an integral inner compression component in the form of an axially-extending sleeve 40. The external diameter of the sleeve 40 is the same as the internal diameter of the wall 31 of the housing 26 and its outer surface is formed with a screw thread form 41 that engages with the screw thread 33 around the wall. The sleeve 40 is longer than the outer collar 35, projecting forwardly beyond its end, being substantially the same length as wall 31 of the housing 26 within which it extends. In the released or unlocked position, shown in FIGS. 1 and 3 the locking ring 34 is in its rearmost position with the two lips 32 and 36 engaged with one another. The sleeve 40 extends about two thirds the way along the wall 31, its forward, patient end being spaced from the base 27. Internally, the sleeve 40 is stepped along its length on its inner surface between a left-hand, rear region 42 and a right-hand, forward region 43. The rear region 42 has an internal diameter slightly larger than the external diameter of the tube 1 so that it is a free sliding fit along the tube. The forward region 43 has a larger internal diameter to form an enlarged recess 44 around the tube 1 and a radially-extending, forward-facing floor or compression surface 45.

The locking arrangement 25 is completed by a compression sleeve or ring 50 made of a compliant, resilient material with a high coefficient of friction such as neoprene. The sleeve 50 has a circular section and is arranged to fit within the recess 44 between the tube 1 and the locking ring 34. In particular, the length of the sleeve 50 is equal, to or slightly less than, the distance between the compression surface 45 on the locking ring 34 and the inside surface or floor 46 of the base 27 so that, when the locking ring 34 is in its rearmost, unlocked position, the compression ring is in its natural, uncompressed state. The internal diameter of the compression sleeve 50 is slightly less than the external diameter of the tube 1 so that, when the ring is in its natural, uncompressed state, the tube can slide freely through the ring. The external diameter of the compression sleeve 50 is equal to the internal diameter of the forward region 43 of the sleeve 40. When the locking ring 34 is in its rearmost, unlocked state the right-hand, forward end of the compression sleeve 50 projects forwardly from the recess 44 beyond the end of the sleeve 40. In this state, the compression ring 50 is uncompressed and the flange 2 with its locking arrangement 25 is released and free to slide along the tube 1 and is free to rotate angularly about the tube 1 so that it can be positioned in the best location for the patient. To lock the flange 2 in the desired position the locking ring 34 is simply twisted clockwise to its full extent into its locking position. In this respect, the locking ring 34 and the housing 26 may be formed with cooperating detents (not shown) at one or both extremes of travel to provide additional resistance to movement out of the fully locked or unlocked positions. The manually-operable means for axially compressing the sleeve 50 need not be a rotatable ring but could take other forms.

Figure 2:
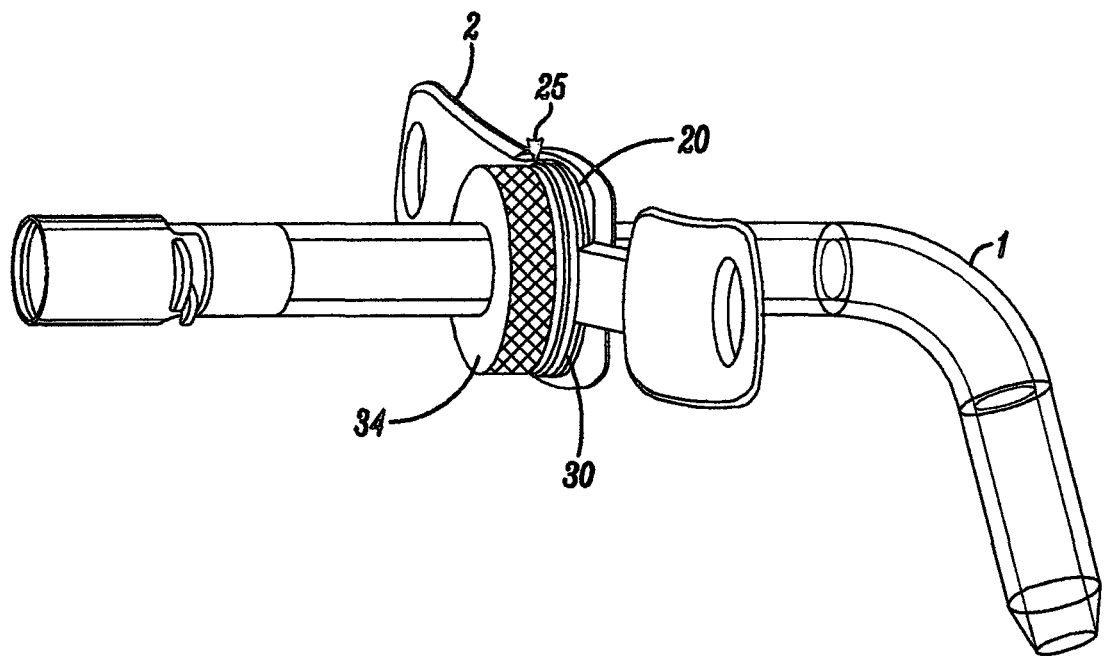
FIG. 2 is a perspective view of the assembly with the flange locked in position.
Figure 4:
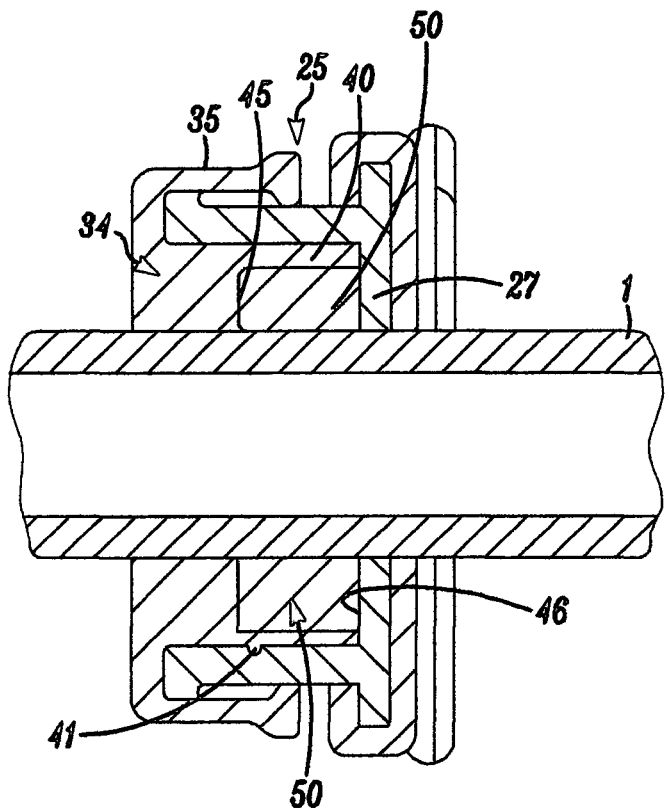
FIG. 4 is a cross-sectional side elevation of the flange in a locked state.

FIGS. 2 and 4 show the tracheostomy tube assembly where the flange assembly 2 is locked in position along the tube 1. It can be seen that the locking ring 34 is in a forward position where the right-hand end of the sleeve 40 is in direct contact with the base 27. The effect of this forward relative displacement of the locking ring 34 is to move the compression surface 45 forwards against the rear face of the compression ring 50. This compresses the ring 50 axially between the compression surface and the floor 46 and thereby results in a force tending to expand the ring radially (Poisson effect) against both the inner surface of the forward region 43 of the sleeve 40 and against the outer surface of the tube 1. The force applied to the outside of the tube 1 is spread over the compressed length of the compression ring 50, typically around 6 mm, so it is distributed over a relatively large area compared with previous arrangements and does not cause any localised indentation in the tube. When the locking ring 34 is released the resilient nature of the compression ring 50 means that it immediately recovers its original shape and any inward compression of the tube 1 also recovers quickly without long term deformation. When in the locked position a high frictional force is exerted on the tube 1 to prevent any slipping. This is due partly to the force exerted on the tube 1 and partly due to the high coefficient of friction of the material from which the compression ring 50 is made. It will be appreciated that it would be possible to make the compression ring from a different material with a relatively low coefficient of friction if the surface contacting the tube were made high friction such as by means of a coating or a thin inner sleeve of a suitable material. This would enable a larger choice of suitable materials, some of which might have better compressibility/resilience properties but have a lower coefficient of friction.

The locking arrangement could be modified by placing one or two low friction washers, such as of metal or PTFE, between the rear end of the compression ring and the compression surface of the locking ring. This would reduce twisting of the compression ring during locking.

The invention is not confined to tracheostomy tubes but could be used with other medico-surgical tubes having a flange for supporting the tube where it emerges from the body.

The invention claimed is:

1. A medico-surgical tube assembly including a tube and a flange assembly movable along the length of the tube, characterised in that the flange assembly includes a locking arrangement including a sleeve of a resilient compressible material extending in a recess of the locking arrangement and arranged to embrace a part of the length of the tube and a manually-operable member mounted with the locking arrangement having a radially-extending compression surface and displaceable between a locking position and a released position, and that the manually-operable member is arranged, when in the released position, to allow free movement of the flange assembly along a part at least of the length of the tube and, when in the locking position, the compression surface applying an axial force to an end of the sleeve such that the sleeve is compressed in length axially and is thereby expanded radially and deformed inwardly into gripping contact with the outside of the tube sufficient to prevent the flange assembly moving along the tube.

2. A medico-surgical tube assembly according to claim 1, characterised in that the manually-operable member is rotatable about the axis of the tube between the locking position and the released position.

3. A medico-surgical tube assembly according to claim 2, characterised in that the manually-operable member is a screw-threaded ring embracing the tube.

4. A medico-surgical tube assembly according to claim 1, characterised in that the sleeve of resilient compressible material is of a neoprene.

5. A medico-surgical tube assembly according to claim 1, characterised in that the manually-operable member and the locking arrangement are provided with cooperating detents arranged to retain the manually-operable member in the locked position.

6. A medico-surgical tube assembly according to claim 1, characterised in that the tube is a tracheostomy tube and the flange assembly has two wings projecting outwardly and each provided with a formation by which opposite ends of a neck strap can be attached to the flange assembly.

7. A medico-surgical tube assembly including a tube and a flange assembly movable along the length of the tube, characterised in that the flange assembly includes a locking arrangement including a housing having a base with an opening through which the tube extends and a cylindrical wall projecting axially of the tube from the base and having an inner surface formed with a screw thread and spaced from the tube, that the locking arrangement further includes a locking ring having an outer collar extending around the outside of the housing and an inner sleeve with a screw thread on its outer surface engaged with the screw thread on the cylindrical wall, that the locking ring defines a radially-extending compression surface and a recess between the inside of the sleeve and the outside of the tube, and that the locking arrangement includes a sleeve of a resilient compressible material located in the recess such that when the locking ring is rotated it moves axially towards the base and the compression surface engages an end of the sleeve of resilient material thereby to compress the sleeve axially along its length so that it is expanded radially and deforms inwardly into gripping contact with the outside of the tube sufficient to prevent the flange assembly moving along the tube.

8. A flange assembly for a medico-surgical tube, characterised in that the flange assembly includes a locking arrangement including a sleeve of a resilient compressible material extending in a recess of the locking arrangement and arranged to embrace a part of the length of the tube and a manually-operable member mounted with the locking arrangement and displaceable between a locking position and a released position, and that the manually-operable member is arranged, when in the released position, to allow free movement of the flange assembly along a part at least of the length of the tube and, when in the locking position, to apply an axial force to an end of the sleeve such that the sleeve is compressed axially along its length so that it expands radially and is thereby deformed inwardly into gripping contact with the outside of the tube sufficient to prevent the flange assembly moving along the tube.

9. A flange assembly according to claim 8, characterised in that the manually-operable member is a screw-threaded ring arranged to embrace the tube and rotatable about the axis of the tube between the locking position and the released position.

10. A flange assembly, which can be fitted onto and be movable along the length of a medico-surgical tube, characterised in that the flange assembly includes a locking arrangement including a housing having a base with an opening through which the tube can extend and a cylindrical wall projecting axially from the base and having an inner surface formed with a screw thread, that the locking arrangement further includes a locking ring having an outer collar extending around the outside of the housing and an inner sleeve with a screw thread on its outer surface engaged with the screw thread on the cylindrical wall, that the locking ring defines a recess between the inside of the sleeve and the outside of the tube and a radially-extending compression surface, and that the locking arrangement includes a sleeve of resilient compressible material located in the recess such that when the locking ring is rotated it moves axially towards the base and the compression surface engages an end of the sleeve of resilient material thereby to compress the sleeve axially along its length so that it is expanded radially and deforms inwardly into gripping contact with the outside of the tube sufficient to prevent the flange assembly moving along the tube.

* * * * *